United States Patent
Kolahi et al.

(10) Patent No.: US 10,337,901 B2
(45) Date of Patent: Jul. 2, 2019

(54) METHOD FOR OPERATING A CORIOLIS MASS FLOWMETER

(71) Applicant: KROHNE Messtechnik GmbH, Duisburg (DE)

(72) Inventors: Kourosh Kolahi, Duisburg (DE); Johannes Kunze, Bochum (DE); Ralf Storm, Essen (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 118 days.

(21) Appl. No.: 15/439,038

(22) Filed: Feb. 22, 2017

(65) Prior Publication Data

US 2017/0241823 A1   Aug. 24, 2017

(30) Foreign Application Priority Data

Feb. 22, 2016   (DE) .................. 10 2016 103 048

(51) Int. Cl.
| | |
|---|---|
| *G01F 1/84* | (2006.01) |
| *G01F 25/00* | (2006.01) |
| *G01N 9/00* | (2006.01) |
| *G01F 15/02* | (2006.01) |

(52) U.S. Cl.
CPC .............. *G01F 1/8436* (2013.01); *G01F 1/84* (2013.01); *G01F 1/849* (2013.01); *G01F 15/02* (2013.01); *G01F 25/00* (2013.01); *G01F 25/0007* (2013.01); *G01N 9/00* (2013.01); *G01N 9/002* (2013.01)

(58) Field of Classification Search
CPC ...... G01F 25/0007; G01F 25/00; G01F 15/02; G01F 1/84; G01F 1/849; G01F 1/8436; G01F 1/8477; G01N 9/00; G01N 9/002
See application file for complete search history.

(56) References Cited

U.S. PATENT DOCUMENTS

| | | |
|---|---|---|
| 6,327,915 B1 | 12/2001 | Van Cleve et al. |
| 7,343,822 B2 | 3/2008 | Kolahi et al. |
| 7,424,376 B2 | 9/2008 | Carpenter |
| 9,322,759 B2 | 4/2016 | Yan et al. |
| 9,592,789 B2 | 3/2017 | Fujiwara |

*Primary Examiner* — Leslie J Evanisko
(74) *Attorney, Agent, or Firm* — David S. Safran; Roberts Mlotkowski Safran Cole & Calderon, P.C.

(57) ABSTRACT

A method for operating a Coriolis mass flowmeter that has at least one measuring tube with medium flowing through it involves exciting the measuring tube excited to oscillation, detecting the oscillations of the measuring tube and determining the density of the medium. Detection of the state and a change in the state of a Coriolis mass flowmeter is achieved by determining a calibration temperature and a calibration density sensitivity of the Coriolis mass flowmeter using the detected oscillations, at a temperature differing from the calibration temperature, and a density sensitivity of the flowmeter determined using the detected oscillations. A measurement rate of change of the density sensitivity is determined and a forecast rate of change of the density sensitivity is calculated using a forecast algorithm, and at a given deviation of the measurement rate of change from the forecast rate of change $r_p$, a deviation signal is generated.

9 Claims, 3 Drawing Sheets

METHOD FOR OPERATING A CORIOLIS MASS FLOWMETER

BACKGROUND OF THE INVENTION

Field of the Invention

The invention relates to a method for operating a Coriolis mass flowmeter, wherein the Coriolis mass flowmeter has at least one measuring tube with medium flowing through it, the measuring tube is excited to oscillation in at least one frequency and/or at least in one eigenform, the resulting oscillations of the measuring tube are detected and the density d of the medium is determined by evaluating the detected oscillations.

Description of Related Art

Methods for operating a Coriolis mass flowmeter do not relate only to processes that deal solely with determining the primary measuring variable, i.e., the mass flow, rather the term is to be understood further. Thus, it is known to also determine the density of the medium flowing through the measuring tube with a Coriolis mass flowmeter, as it is described in the publication of the European patent application EP 1 659 389 A1 corresponds to U.S. Pat. No. 7,343,822 B2. The determination of the density is carried out by evaluating the oscillations of the measuring tube. Other methods for operating a Coriolis mass flowmeter are aimed at determining the pressure of the medium, wherein this can also take place using a mathematical model of the Coriolis mass flowmeter, i.e. without having to directly measure the pressure.

Other methods deal with recognizing multi-phase flows, i.e., a state of flow in the measuring tube that requires a quick readjustment of excitation frequencies and amplitudes of the oscillations of the measuring tube.

The above methods have the advantage that a large amount of information about the variables of the process, with which the Coriolis mass flowmeter communicates, can be obtained.

SUMMARY OF THE INVENTION

A primary object of the present invention is to further develop the method for operating a Coriolis mass flowmeter on which the invention is based in such a manner that statements can be made about the state of the Coriolis mass flowmeter, so that, for example, a change of the system behavior of the Coriolis mass flowmeter can be recognized.

The above-described object is achieved by the method for operating a Coriolis niass flowmeter mentioned in the introduction, in that at a calibration temperature $T_k$, a calibration density sensitivity $E_{d,k}(T_k)$ of the Coriolis mass flowmeter is determined using the detected oscillations of the measuring tube, that, at a temperature T differing from the calibration temperature $T_k$, a density sensitivity $E_d(T)$ of the Coriolis mass flowmeter is determined using the detected oscillations of the measuring tube, that a measurement rate of change $r_m$ of the density sensitivity $E_d$ is determined using the calibration density sensitivity $E_{d,k}(T_k)$ determined using the detected oscillations and the density sensitivity $E_d(T)$ at the temperature T, that a forecast rate of change $r_p$ of the density sensitivity is calculated using a forecast algorithm, which is dependent on the temperature T differing from the calibration temperature $T_k$, however, which does not depend on the detected oscillations of the measuring tube, and that, at a given deviation of the measurement rate of change $r_m$ from the forecast rate of change $r_p$, a deviation signal is generated.

The basic idea of the method according to the invention is that a change in the rate of change r of the density sensitivity $E_d$ of the Coriolis mass flowmeter is recognized in dependence on the temperature and is subsequently issued as an indication of a—usually unwanted—change on the Coriolis mass flowmeter.

When density sensitivity is being discussed here, then what is meant is the sensitivity with which the determined density d of the medium changes in dependence on a relevant variable. In determining the density d of the medium, the basic correlation between the resonance frequency $f_0$ of the measuring tube with medium flowing through it and the density d of the medium is used in Coriolis mass flowmeters. Such a correlation is shown in equation:

$$d = E_d \cdot \omega_0^{-2} - d_{off} \qquad (1)$$

$\omega_0$ is the angular resonance frequency, which differs from the resonance frequency $f_0$ only by the factor $2\pi$. $d_{off}$ is an offset value for the density d in the equation. The density sensitivity $E_d$ is, thus, the sensitivity with which the density d of the medium changes at a change of the detected resonance frequency $f_0$.

It is known that the density sensitivity $E_d$ of the Coriolis mass flowmeter is dependent on the temperature of the measuring tube and the temperature of the medium, wherein the temperature of the medium and the temperature of the measuring tube can be practically be assumed as being the same, which is why, in the following, only one temperature T is mentioned.

In the first mentioned method step, the calibration density sensitivity $E_{d,k}$ is determined at a known calibration temperature $T_k$, i.e. simply the density sensitivity $E_d$ at the calibration temperature $T_k$. The determination of the calibration density sensitivity $E_{d,k}$ for the Coriolis mass flowmeter can only be carried out once, normally, the calibration density sensitivity $E_{d,k}$ is stored together with the calibration temperature $T_k$. The values can be recorded in the scope of factory calibration if the opportunity exists, but can also take place in the assembly situation in the process.

When the state of the Coriolis mass flowmeter is to be checked, a current density sensitivity $E_d$ of the Coriolis mass flowmeter is always determined at a temperature T differing from the calibration temperature $T_k$. It is important that both the calibration density sensitivity $E_{d,k}$ as well as the density sensitivity $E_d$ typically determined at another point in time are made at a differing temperature T using the detected oscillations of the measuring tube. This is important because the oscillations of the measuring tube are characteristic for the state of the Coriolis mass flowmeter. A measurement rate of change $r_m$ of the density sensitivity $E_d$ can be determined from the two density sensitivities $E_d$ that were determined using the detected oscillations, i.e. the change of the density sensitivity $E_d$ in dependence on the temperature or, respectively, the temperature difference. The term "measurement rate of change" indicates that this rate of change of the density sensitivity is based on the detected—i.e. measured—oscillations of the measuring tube of the Coriolis mass flowmeter.

Additionally, a further rate of change of the density sensitivity $E_d$ is determined, namely a forecast rate of change $r_p$. A forecast algorithm that depends on the current temperature T differing from the calibration temperature $T_k$ is used for this. It is important that this forecast algorithm—regardless of how it is determined—is not dependent on the detected oscillations of the measuring tube.

The forecast algorithm for the forecast rate of change $r_p$ of the density sensitivity is advantageously determined when the calibration density sensitivity $E_{d,k}$ of the Coriolis mass flowmeter is also determined. This is a calculation rule that makes it possible to determine the rate of change of the density sensitivity in dependence on the temperature T, i.e. the forecast algorithm reproduces the rate of change of the density sensitivity in an original state of the Coriolis mass flowmeter. Changes in the system behavior of the Coriolis mass flowmeter are not able to influence the determination of the forecast rate of change $r_p$ of the density sensitivity, since the forecast algorithm intentionally does not depend on the detected oscillations of the measuring tube.

Finally, the two determined rates of the change of density sensitivity are compared to one another, wherein a deviation of the measurement rate of change $r_m$ from the forecast rate of change $r_p$ of the density sensitivity indicates a change of the dynamic behavior of the Coriolis mass flowmeter. Such a change can, for example, be based on a structural change of the measuring tube due to wear or due to deposition of material in the measuring tube. If a deviation of the measurement rate of change $r_m$ from the forecast rate of change $r_p$ is discovered, or this deviation exceeds a certain threshold, a deviation signal is generated that indicates this change in the behavior of the Coriolis mass flowmeter. The deviation signal can be information stored in the Coriolis mass flowmeter, the signal can be shown on a display of the Coriolis mass flowmeter, it can also be issued via an interface of the Coriolis mass flowmeter via a databus.

According to an advantageous implementation of the method, it is provided that the measurement rate of change $r_m$ is calculated by forming the quotient of the density sensitivity $E_d(T)$ determined at the temperature T and the density sensitivity $E_d(T_k)$ determined at the calibration temperature $T_k$. The determination of the measurement rate of change $r_m$ is then carried out according to the following equation:

$$r_m = E_d(T)/E_{d,k}(T_k).$$

In one implementation of the above described method, it is provided that the density sensitivity $E_d$ is determined by means of a mathematical model $G_1(s)$ of the Coriolis mass flowmeter of at least second order, in that the measuring tube is excited to oscillation in the first eigenform at an eigenfrequency $f_{01}$ and a two additional frequencies $f_{ZA}$ and $f_{ZB}$. The description of Coriolis mass flowmeters with the help of mathematical models, which are based on differential equations of at least second order, is extensively known, for example from the previously mentioned EP 1 659 389 A1. A specific calculation rule, with which the density sensitivity can be calculated using three excitation frequencies is, for example:

$$E_d = \frac{\omega_{ZB}\omega_{ZA}}{V_F(\omega_{ZB}^2 - \omega_{ZA}^2)} \frac{\omega_{ZB} \, \text{Im}\{G_1(j\omega_{ZA})\}}{\text{Im}\{G_1(j\omega_{ZA})\}^2 + \text{Re}\{G_1(j\omega_{ZA})\}^2} - \frac{\omega_{ZB}\omega_{ZA}}{V_F(\omega_{ZB}^2 - \omega_{ZA}^2)} \frac{\omega_{ZA} \, \text{Im}\{G_1(j\omega_{ZB})\}}{\text{Im}\{G_1(j\omega_{ZB})\}^2 + \text{Re}\{G_1(j\omega_{ZB})\}^2} \quad (2)$$

$G_1(s)$ is the complex transfer function for describing the movement of the measuring tube in an eigenform, presently, the first eigenform. $\omega_{ZA}$ and $\omega_{ZB}$ are the angular frequencies corresponding to the frequencies $f_{ZA}$ and $f_{ZB}$. Here, $V_F$ is the volume of the measuring tube. The first eigenform is the excitation mode of the measuring tube at central deflection, in which, for example, a straight measuring tube forms a central antinode. The shown procedure fulfills the requirement that the density sensitivity is determined using the detected oscillations of the measuring tube.

A further advantageous implementation of the method according to the invention is wherein the forecast algorithm for the forecast rate of change $r_p$ is a polynomial in the temperature difference of the temperature T differing from the calibration temperature $T_k$ and the calibration temperature $T_k$, in particular wherein the forecast algorithm for the forecast rate of change $r_p$ is a linear polynomial in the temperature difference. The forecast algorithm, i.e. the calculation rule for the forecast rate of change $r_p$, in this case, looks like the following:

$$r_p = r_p(T-T_k) = 1 + r_{p0}^*(T-T_k)$$

This calculation rule also fulfills the requirement that it is not dependent on the detected oscillations of the measuring tube and, in this respect, changes in the system dynamics of the Coriolis mass flowmeter are not able to affect the determination of the forecast rate of change $r_p$.

The factor $r_{p0}$ of the linear member of the temperature difference $(T-T_k)$ can be determined in various manners. In one design of the method, it is provided that the factor $r_{p0}$ of the linear member of the temperature difference $(T-T_k)$ is determined by determining at least two density sensitivities $E_d$ at at least two different temperatures, of which one temperature is the calibration temperature $T_k$.

Coriolis mass flowmeters in normal operation, i.e. in their measurement operation mode, are normally excited with a maximum amplitude in view of measuring tube oscillation. In this manner, a good signal to noise ratio in the detection of the oscillations of the measuring tube is achieved. In a further advantageous implementation of the method according to the invention, this method is carried out in a test mode, in which the measuring tube is excited to oscillations with an amplitude reduced in comparison to the measurement operation mode. This makes is possible to excite the measuring tube simultaneously with different frequencies, for example with the resonance frequency of the first eigenform and the two frequencies outside of the resonance differing from it.

Preferably, the oscillation of the measuring tube in the second eigenform is evaluated simultaneously with the execution of the previously described method and, on the basis of this information, the mass flow is determined in the usual manner for Coriolis mass flowmeters. The Coriolis mass flowmeter is, thus, then simultaneously operated in its measurement operation mode as well as in its test mode. This makes it possible, during the continuous determination of the mass flow, to obtain information about a changed state of the Coriolis mass flowmeter using the determination of the rate of change of the density sensitivity. When the test mode is carried out with several frequencies, each having a reduced amplitude, then the signal to noise ratio is certainly reduced for the determination of the mass flow, but the measurement operation does not have to be interrupted.

In a further advantageous implementation of the method, it is provided that at least one of the method steps of determining the calibration density sensitivity $E_{d,k}(T_k)$, determining the density sensitivity $E_d(T)$ at a temperature T differing from the calibration temperature $T_k$, determining the measurement rate of change $r_m$ of the density sensitivity $E_d$, determining the forecast rate of change $r_p$ of the density sensitivity using a forecast algorithm, and generating a deviation signal is carried out in a test device to be attached to the Coriolis mass flowmeter. It is of particular advantage when all above method steps except determining the calibration density sensitivity are implemented in the test device to be attached to the Coriolis mass flowmeter. Preferably, the calibration density sensitivity $E_{d,k}$ and the calibration temperature as well as a clear description of the forecast algorithm for the forecast rate of change $r_p$ is stored in the respective Coriolis mass flowmeter, since this information is characteristic for the individual mass flowmeter. For example, the parameter $r_{p0}$ could be stored in the Coriolis mass flowmeter. The test device is then designed so that it determines the density sensitivity $E_d(T)$ at temperature T, that it determines the measurement rate of change $r_m$ of the density sensitivity $E_d$ from the calibration density sensitivity $E_{d,k}(T_k)$ and the density sensitivity $E_d(T)$ at temperature T, that it calculates a forecast rate of change $r_p$ of the density sensitivity using a forecast algorithm and that it generates a deviation signal when a predetermined deviation of the measurement rate of change $r_m$ from the forecast rate of change $r_p$ is exceeded.

The method according to the invention is preferably applied so that the determination of the calibration density sensitivity $E_{d,k}(T_k)$ and the determination of the forecast algorithm for the forecast rate of change $r_p$ are carried out at a point in time before start-up of the Coriolis mass flowmeter in the process, in particular during factory calibration of the Coriolis mass flowmeter.

In detail, there is a plurality of possibilities for designing and further developing the method according to the invention for operating a Coriolis mass flowmeter. Reference is made to the following description of preferred embodiments of the invention in respect to the drawings.

DETAILED DESCRIPTION OF THE INVENTION

Figure 1:
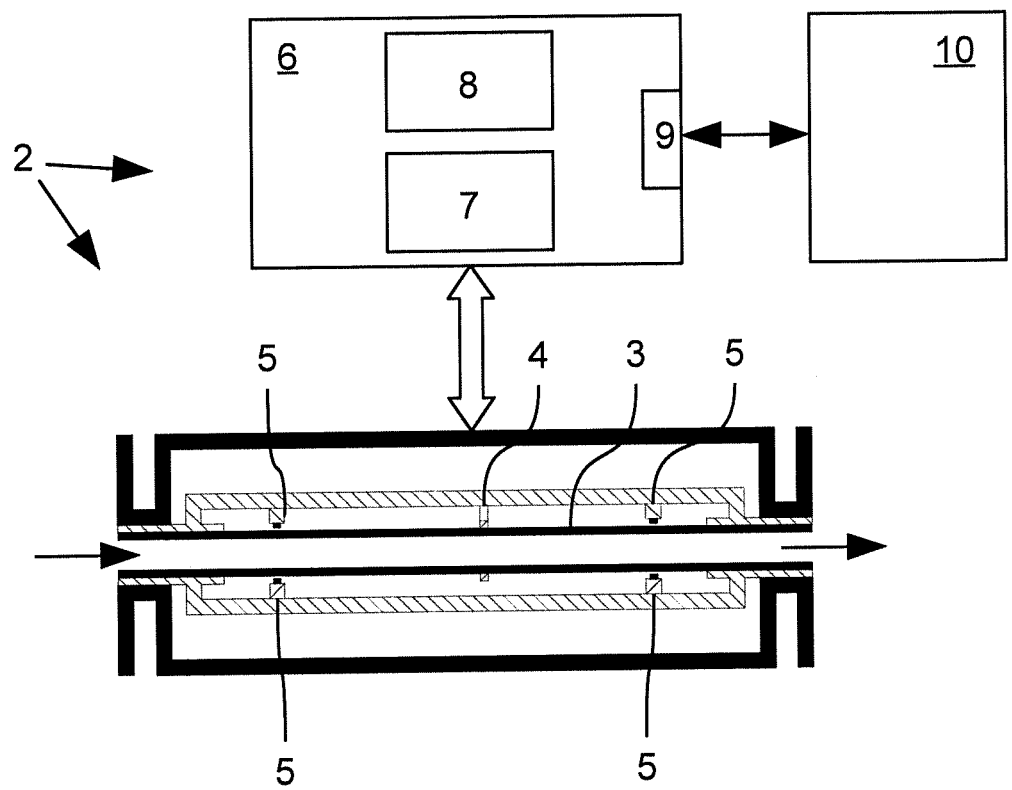
FIG. 1 schematically shows a Coriolis mass flowmeter, with which the method of the invention is carried out.
Figure 2:
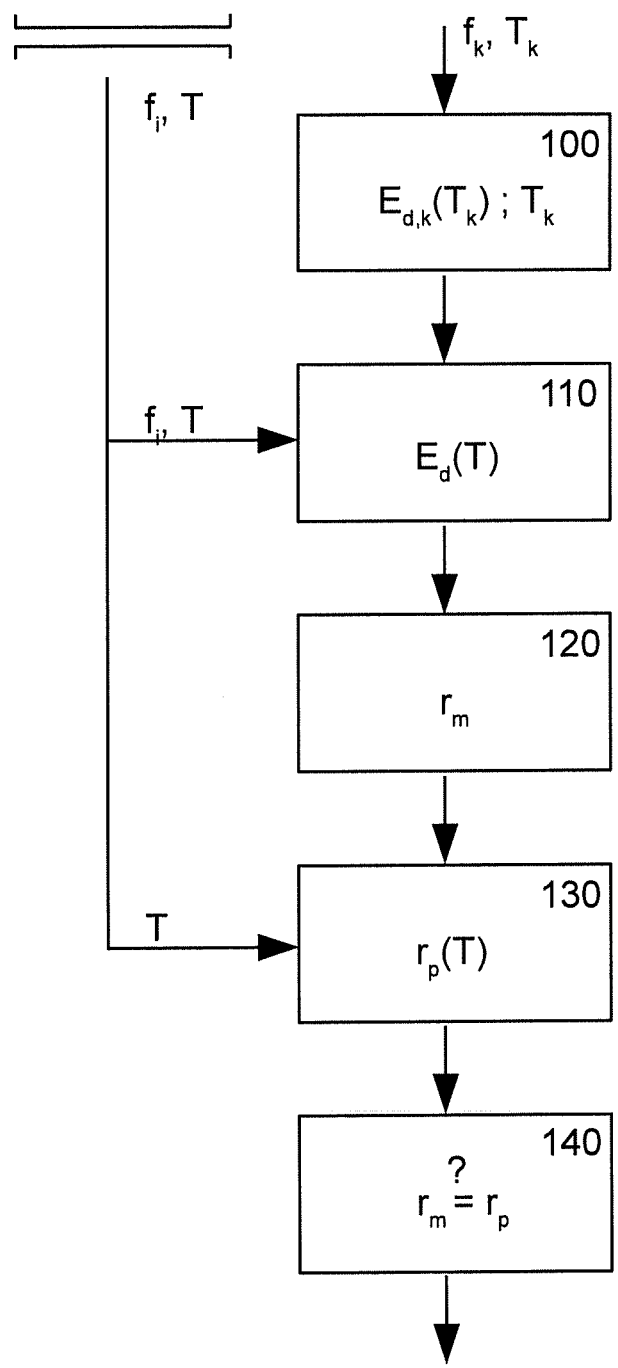
FIG. 2 is a flow chart of the method of the invention for operation a Coriolis mass flowmeter.
Figure 3:
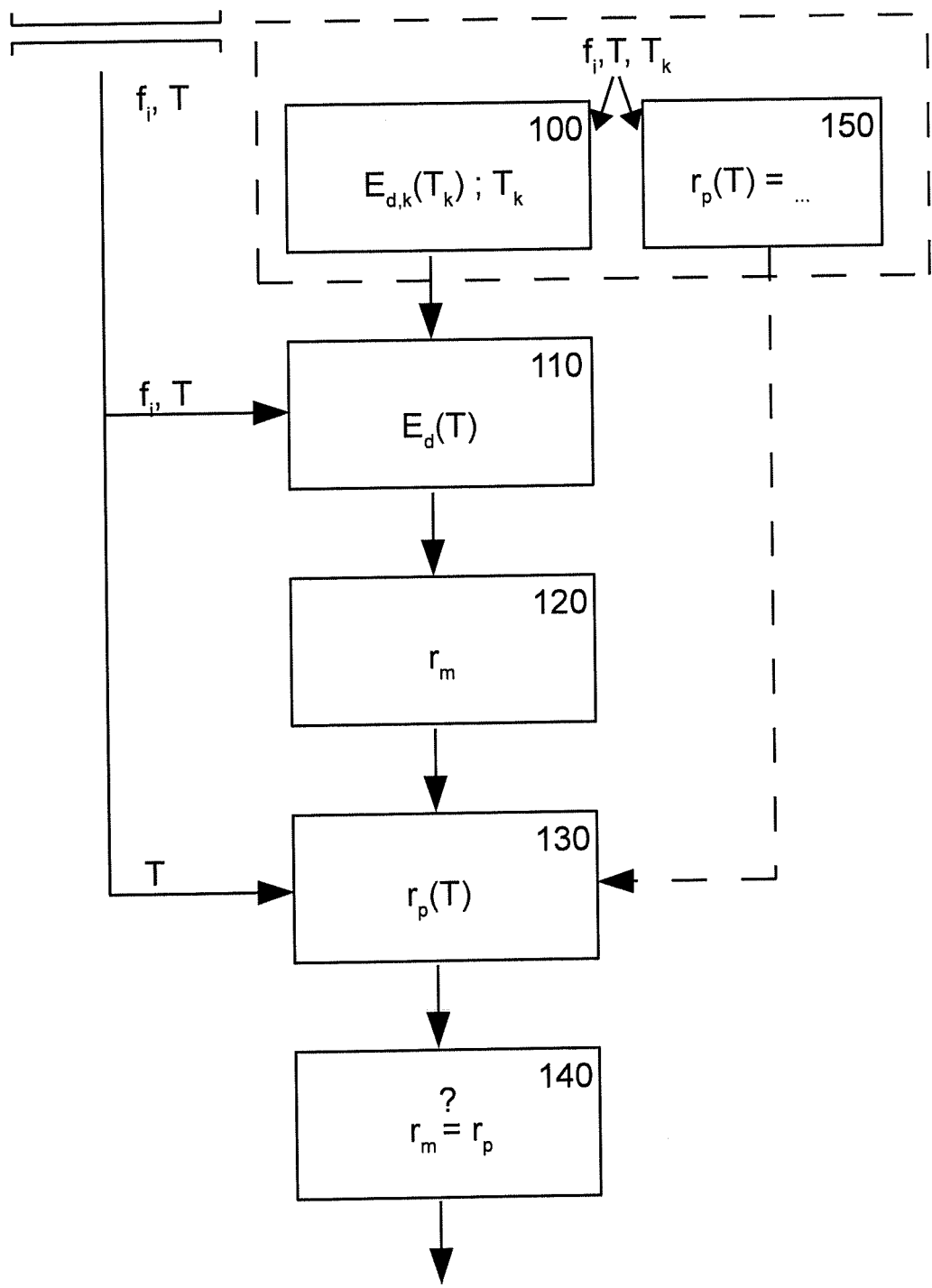
FIG. 3 is a flow chart, enhanced compared to the representation in FIG. 2, for illustrating the method of the invention.

In FIGS. 1 to 3, a method for operating a Coriolis mass flowmeter 2 is basically shown, wherein FIG. 1 essentially addresses the structural design of the Coriolis mass flowmeter 2. The Coriolis mass flowmeter 2 has a measuring tube 3 with a medium that is not shown in detail flowing through it.

The measuring tube 3 is excited to oscillations in at least one frequency and/or in at least one eigenform. An electromagnetic actuator 4 arranged centrally in respect to the longitudinal extension of the measuring tube 3 is used for this, with which a force can be exerted centrally on the measuring tube 3, with which the measuring tube 3 is excited into a first oscillation mode. When medium is flowing through the measuring tube 3, an oscillation of the measuring tube 3 in the second oscillation mode is automatically engaged due to the operative Coriolis forces, this is sometimes also called the Coriolis mode.

The resulting oscillations of the measuring tube 3 can be detected by means of the oscillation sensors 5 arranged to the left and right of the actuator 4. Different measuring variables can be determined by evaluating the measuring tube oscillations. The primary measuring variable, i.e., the mass flow, can be determined by evaluating the oscillations in the second eigenform of the measuring tube 3. The density of the medium can be determined by evaluating the measuring tube oscillations in the first eigenform, as is generally known.

In addition to the mechanical construction, the Coriolis mass flowmeter 2 also has an electronic control and evaluation unit 6, which is usually integrated in a standard housing of the Coriolis mass flowmeter 2, which is not shown here. The control and evaluation unit 6 is used, on the one hand, for properly controlling the measuring tube 3 of the Coriolis mass flowmeter 2 with a control signal, for updating the excitation frequency into the resonance frequency of the measuring tube 3, for setting a frequency intentionally deviating from the resonance frequency, for evaluating the sensor signal of the oscillation sensors 5 as well as for carrying out different methods for operating the Coriolis mass flowmeter such as determining primary measuring variables, determining secondary measuring variables and observing the Coriolis mass flowmeter 2. To this end, the control and evaluation unit 6 is provided with an electronic computing unit 7 and, in the present case, with a display unit 8. Data can be exchanged between the Coriolis mass flowmeter 2 and an external device 10 via an interface 9. The external device 10 can be a control center, an operating device or also a test device.

The claimed method for operating the Coriolis mass flowmeter 2 is shown in FIGS. 2 and 3. The idea of the method consists of determining rates of change r of the density sensitivity $E_d$ for testing the Coriolis mass flowmeter 2 and a deviation from the rate of change r being an indication of a change of the dynamic behavior of the Coriolis mass flowmeter 2.

To this end, a rate of change r of the density sensitivity $E_d$, namely the measurement rate of change $r_m$ is determined in dependence on the detected oscillations of the measuring tube 3, so that changed system dynamics also affect the determination of the measurement rate of change $r_m$.

Another rate of change of the density sensitivity, namely the forecast rate of change $r_p$, is also determined, wherein the forecast algorithm for calculating this forecast rate of change $r_p$ is not dependent on the detected oscillations of the measuring tube 3 and thus not on changed system dynamics of the Coriolis mass flowmeter 2. In this manner, conclusions can be made about the the state or, respectively about a changed state of the Coriolis mass flowmeter 2 based on the determination of the rate of the change of the sensitivity of density measurement.

The measuring tube 3 is shown initially schematically and representatively for the entire Coriolis mass flowmeter 2 in FIGS. 2 and 3. Oscillations are detected from the measuring tube 3 that have one or several frequencies $f_i$. Furthermore, the measuring tube has a temperature T.

In method step 100, the calibration density sensitivity $E_{d,k}$ of the Coriolis mass flowmeter 2 is determined at a calibration temperature $T_k$ using the detected oscillations of the measuring tube 3. This is indicated in FIGS. 2 and 3 by the detected measuring tube oscillation with the frequency $f_k$ and the temperature $T_k$.

In the method step 110, the density sensitivity $E_d(T)$ of the Coriolis mass flowmeter 2 is determined at a temperature T differing from the calibration temperature $T_k$ using the detected oscillations of the measuring tube 3. Since the determination of the density sensitivity $E_d(T)$ takes place using the detected oscillations of the measuring tube 3, the density sensitivity $E_d(T)$ is dependent on the dynamic behavior of the Coriolis mass flowmeter 2 or, respectively, the measuring tube 3.

In method step 120, using the previously-obtained data, a measurement rate of change $r_m$ of the density sensitivity $E_d$ is determined from the calibration density sensitivity $E_{d,k}(T_k)$ and the density sensitivity $E_d(T)$. In the present case, the quotient of these two density sensitivities is formed.

In the subsequentially shown method step 130, a forecast rate of change $r_p$ of the density sensitivity $E_d$ is calculated with a forecast algorithm, which, namely, is dependent on the temperature T differing from the calibration temperature $T_k$, however is not dependent on the detected oscillations of the measuring tube 3, which is indicated in that only the temperature T affects the determination of the forecast rate of change $r_p$.

Finally, in the method step 140, a deviation of the measurement rate of change $r_m$ from the forecast rate of change $r_p$ is determined and, in the case of a deviation or the exceedance of a certain deviation threshold, a deviation signal is generated.

In FIGS. 2 and 3, a sequence of all method steps 100, 110, 120, 130, 140 is shown. This does not necessarily have to be so. In fact, the forecast rate of change $r_p$ can be calculated independently from the previously shown method steps, i.e., for example, simultaneously with these method steps. It is only required for the last method step of determining a deviation of the measurement rate of change $r_m$ from the forecast rate of change $r_p$ that these rates of change are known in full.

It is shown in FIG. 3 that the determination of the calibration density sensitivity $E_{d,k}(T_k)$ in method step 100 and the determination of the forecast algorithm for determining the forecast rate of change $r_p$ of the density sensitivity $E_d$ in preliminarily take place in a method step 150, preferably during calibration of the Coriolis mass flowmeter 2, for example during initial factory calibration. The corresponding data are then preferably stored in the Coriolis mass flowmeter, since they characterize the individual Coriolis mass flowmeter.

What is claimed is:

1. A method for operating a Coriolis mass flowmeter, wherein the Coriolis mass flowmeter has at least one measuring tube with medium flowing through it, and an electronic control and evaluation unit for controlling the measuring tube with a control signal and for setting excitation frequencies, the method comprising in an operation mode of the Coriolis mass flow meter:

exciting the at least one measuring tube to oscillation in at least one frequency and/or in at least one eigenform, using oscillation sensors for detecting oscillations of the measuring tube, and using the electronic control and evaluation unit for determining a density of the medium by evaluating the detected oscillations, wherein:

at a calibration temperature, a calibration density sensitivity of the Coriolis mass flowmeter is determined by the electronic control and evaluation unit using oscillations of the measuring tube detected by the oscillation sensors, at a temperature that differs from the calibration temperature and which is independent of the detected oscillations of the measuring tube, a density sensitivity of the Coriolis mass flowmeter is determined by the electronic control and evaluation unit using the oscillations of the measuring tube detected by the oscillation sensors, a measurement rate of change of density sensitivity is determined by the electronic control and evaluation unit using the calibration density sensitivity determined using the detected oscillations and the density sensitivity at the temperature, a forecast rate of change of the density sensitivity is calculated by the control and evaluation unit using a forecast algorithm which is dependent on the temperature, and at a given deviation of the measurement rate of change from the forecast rate of change, exceeds a certain threshold, a deviation signal is generated by the electronic control and evaluation unit which indicates an unwanted change in a dynamic system behavior of the Coriolis mass flowmeter due to a structural change of the measuring tube due to at least one of wear of the measuring tube or deposition of material in the measuring tube.

2. A method according to claim 1, wherein the measurement rate of change is determined by formation of a quotient from the density sensitivity determined at the temperature and from the density sensitivity determined at the calibration temperature using the electronic control and evaluation unit.

3. A method according to claim 1, wherein the density sensitivity is determined by means of a mathematical model of the Coriolis mass flowmeter of at least second order in that the measuring tube is excited to oscillation in a first eigenform at an eigenfrequency of the first eigenform and at two additional frequencies.

4. A method according to claim 1, wherein the forecast algorithm for the forecast rate of change is a polynomial of a temperature difference of the temperature from the calibration temperature.

5. A method according to claim 4, wherein a factor of a linear member of the temperature difference is determined by determining at least two density sensitivities at at least two different temperatures, of which one temperature is the calibration temperature.

6. A method according to claim 1, wherein the method is carried out in a test mode, in which the measuring tube is excited to oscillation with an amplitude that is less than in the measurement operating mode.

7. A method according to claim 1, wherein evaluation of the oscillation of the measuring tube in a second eigenform takes place simultaneously with determination of the mass flow through the measuring tube.

8. A method according to claim 1, wherein at least one of the method steps of determining the calibration density sensitivity, determining the density sensitivity at a temperature differing from the calibration temperature, determining the measurement rate of change of the density sensitivity, determining the forecast rate of change of the density sensitivity using a forecast algorithm, and generating of a deviation signal is carried out in a test mode using a test device attached to the Coriolis mass flowmeter, the test mode being performable simultaneously with the operational mode.

9. A method according to claim 1, wherein determining the calibration density sensitivity and determining the forecast algorithm for the forecast rate of change are carried out during factory calibration of the Coriolis mass flowmeter.

* * * * *